US007806839B2

(12) United States Patent
Mast et al.

(10) Patent No.: US 7,806,839 B2
(45) Date of Patent: Oct. 5, 2010

(54) SYSTEM AND METHOD FOR ULTRASOUND THERAPY USING GRATING LOBES (75) Inventors: T. Douglas Mast, Cincinnati, OH (US); Waseem Faidi, Clifton Park, NY (US); Inder Raj S. Makin, Loveland, OH (US); Peter G. Barthe, Phoenix, AZ (US); Michael H. Slayton, Tempe, AZ (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 915 days.

(21) Appl. No.: 10/867,170

(22) Filed: Jun. 14, 2004

(65) Prior Publication Data
US 2005/0277853 A1  Dec. 15, 2005

(51) Int. Cl.
  *A61H 1/00* (2006.01)
  *A61H 1/02* (2006.01)
  *A61H 5/00* (2006.01)
(52) U.S. Cl. .......................................... 601/2
(58) Field of Classification Search ............ 601/2; 600/437, 439
  See application file for complete search history.

(56) References Cited
U.S. PATENT DOCUMENTS

| | | | |
|---|---|---|---|
| 3,168,659 A | 2/1965 | Bayre et al. | |
| 3,779,234 A | 12/1973 | Eggleton et al. | |
| 3,902,501 A | 9/1975 | Citron et al. | |
| 3,927,557 A | 12/1975 | Viertl | |
| 4,211,948 A * | 7/1980 | Smith et al. | 310/322 |
| 4,315,514 A | 2/1982 | Drewes et al. | |
| 4,323,077 A | 4/1982 | Smith | |
| 4,484,569 A | 11/1984 | Driller et al. | |
| 4,646,756 A | 3/1987 | Watnough et al. | |
| 4,748,985 A | 6/1988 | Nagasaki | |
| 4,757,820 A | 7/1988 | Itoh | |
| 4,787,394 A | 11/1988 | Ogura | |
| 4,790,329 A | 12/1988 | Simon | |
| 4,798,215 A | 1/1989 | Turner | |
| 4,818,954 A | 4/1989 | Flachenecker et al. | |

(Continued)

FOREIGN PATENT DOCUMENTS

EP  0897696  2/1999

(Continued)

OTHER PUBLICATIONS

Christensen, D. A., Ultrasonic Bioinstrumentation, 1988, John Wiley and Sons, p. 105, p. 155.*

(Continued)

*Primary Examiner*—Long V Le
*Assistant Examiner*—Jacqueline Cheng
(74) *Attorney, Agent, or Firm*—Verne E. Kreger, Jr.

(57) ABSTRACT

A system and method for medical treatment of tissue using ultrasound. The system comprises a probe having an array of transducer elements, an ultrasound waveform generator adapted to generate at least one electrical ultrasound signal, and a plurality of phase controls, each coupled to the ultrasound waveform generator and adapted to generate from the electrical ultrasound signal a phase-shifted drive signal that is coupled to an associated transducer element. The drive signal is effective to control grating lobe foci emitted by the array. The method employs the system.

6 Claims, 5 Drawing Sheets

U.S. PATENT DOCUMENTS

| | | |
|---|---|---|
| 4,844,080 A | 7/1989 | Frass et al. |
| 4,858,613 A | 8/1989 | Fry et al. |
| 4,932,414 A | 6/1990 | Coleman et al. |
| 4,937,767 A | 6/1990 | Reuschel et al. |
| 4,951,653 A | 8/1990 | Fry et al. |
| 4,955,365 A | 9/1990 | Fry et al. |
| 4,955,366 A | 9/1990 | Uchiyama et al. |
| 4,960,107 A | 10/1990 | Aida et al. |
| 4,960,109 A | 10/1990 | Lele |
| 4,984,575 A | 1/1991 | Uchiyama et al. |
| 4,986,275 A | 1/1991 | Ishida et al. |
| 5,005,580 A | 4/1991 | Okazaki |
| RE33,590 E | 5/1991 | Dory |
| 5,015,929 A | 5/1991 | Cathignol et al. |
| 5,031,626 A | 7/1991 | Hassler et al. |
| 5,036,855 A | 8/1991 | Fry et al. |
| 5,042,486 A | 8/1991 | Pfeiler et al. |
| 5,054,470 A | 10/1991 | Fry et al. |
| 5,065,740 A | 11/1991 | Itoh |
| 5,078,144 A | 1/1992 | Sekino et al. |
| 5,080,101 A | 1/1992 | Dory |
| 5,080,102 A | 1/1992 | Dory |
| 5,095,906 A | 3/1992 | Ema |
| 5,095,907 A | 3/1992 | Kudo et al. |
| 5,117,832 A | 6/1992 | Sanghvi et al. |
| 5,143,073 A | 9/1992 | Dory |
| 5,143,074 A | 9/1992 | Dory |
| 5,148,809 A | 9/1992 | Biegeleisen-Knight et al. |
| 5,149,319 A | 9/1992 | Unger |
| 5,150,711 A | 9/1992 | Dory |
| 5,150,712 A | 9/1992 | Dory |
| 5,158,070 A | 10/1992 | Dory |
| 5,158,071 A | 10/1992 | Umemura et al. |
| 5,203,333 A | 4/1993 | Nomura |
| 5,209,221 A | 5/1993 | Riedlinger |
| 5,238,007 A | 8/1993 | Giele et al. |
| 5,240,005 A | 8/1993 | Viebach |
| 5,242,437 A | 9/1993 | Everett et al. |
| 5,295,484 A | 3/1994 | Marcus et al. |
| 5,304,115 A | 4/1994 | Pflueger et al. |
| 5,311,869 A | 5/1994 | Okazaki |
| 5,345,940 A | 9/1994 | Seward et al. |
| 5,348,017 A | 9/1994 | Thornton et al. |
| 5,354,258 A | 10/1994 | Dory |
| 5,370,121 A | 12/1994 | Reichenberger et al. |
| 5,391,140 A | 2/1995 | Schaetzle et al. |
| 5,391,197 A | 2/1995 | Burdette et al. |
| 5,398,690 A | 3/1995 | Batten et al. |
| 5,398,691 A | 3/1995 | Martin et al. |
| 5,402,792 A | 4/1995 | Kimura |
| 5,409,002 A | 4/1995 | Pell |
| 5,419,335 A | 5/1995 | Hartmann et al. |
| 5,421,338 A | 6/1995 | Crowley et al. |
| 5,431,663 A | 7/1995 | Carter |
| 5,435,304 A | 7/1995 | Oppelt et al. |
| 5,435,311 A | 7/1995 | Umemura et al. |
| 5,443,069 A | 8/1995 | Schaetzle |
| 5,448,994 A | 9/1995 | Iinuma |
| 5,458,597 A | 10/1995 | Edwards et al. |
| 5,465,724 A | 11/1995 | Sliwa et al. |
| 5,471,988 A | 12/1995 | Fujio et al. |
| 5,474,071 A | 12/1995 | Chapelon et al. |
| 5,485,839 A | 1/1996 | Aida et al. |
| 5,492,126 A | 2/1996 | Hennige et al. |
| 5,500,012 A | 3/1996 | Brucker et al. |
| 5,501,655 A | 3/1996 | Rolt et al. |
| 5,514,085 A | 5/1996 | Yoon |
| 5,514,130 A | 5/1996 | Baker |
| 5,520,188 A | 5/1996 | Hennige et al. |
| 5,522,869 A | 6/1996 | Burdette et al. |
| 5,524,620 A | 6/1996 | Rosenschein |
| 5,526,815 A | 6/1996 | Granz et al. |
| 5,526,816 A | 6/1996 | Arditi |
| 5,526,822 A | 6/1996 | Burbank et al. |
| 5,540,656 A | 7/1996 | Pflueger et al. |
| 5,545,195 A | 8/1996 | Lennox et al. |
| 5,547,459 A | 8/1996 | Kaufman et al. |
| 5,549,638 A | 8/1996 | Burdette |
| 5,553,618 A | 9/1996 | Suzuki et al. |
| 5,558,092 A | 9/1996 | Unger et al. |
| 5,569,241 A | 10/1996 | Edwards |
| 5,571,088 A | 11/1996 | Lennox et al. |
| 5,573,497 A | 11/1996 | Chapelon |
| 5,575,288 A | 11/1996 | Sliwa et al. |
| 5,575,772 A | 11/1996 | Lennox |
| 5,575,789 A | 11/1996 | Bell et al. |
| 5,582,588 A | 12/1996 | Sakurai et al. |
| 5,588,432 A | 12/1996 | Crowley |
| 5,590,657 A * | 1/1997 | Cain et al. ................. 600/439 |
| 5,596,991 A | 1/1997 | Tanaka |
| 5,601,526 A | 2/1997 | Chapelon et al. |
| 5,603,326 A | 2/1997 | Richter |
| 5,606,975 A | 3/1997 | Liang et al. |
| 5,620,479 A | 4/1997 | Diederich |
| 5,624,382 A | 4/1997 | Oppelt et al. |
| 5,626,607 A | 5/1997 | Malecki et al. |
| 5,628,743 A | 5/1997 | Cimino |
| 5,630,837 A | 5/1997 | Crowley |
| 5,643,179 A | 7/1997 | Fujimoto |
| 5,649,547 A | 7/1997 | Ritchart et al. |
| 5,657,760 A | 8/1997 | Ying et al. |
| 5,665,054 A | 9/1997 | Dory |
| 5,666,954 A | 9/1997 | Chapelon et al. |
| 5,676,692 A | 10/1997 | Sanghvi et al. |
| 5,687,729 A | 11/1997 | Schaetzle |
| 5,694,936 A | 12/1997 | Fujimoto et al. |
| 5,697,897 A | 12/1997 | Buchholtz et al. |
| 5,699,804 A | 12/1997 | Rattner |
| 5,699,805 A | 12/1997 | Seward et al. |
| 5,703,922 A | 12/1997 | Rattner |
| 5,715,825 A | 2/1998 | Crowley |
| 5,720,287 A | 2/1998 | Chapelon et al. |
| 5,722,411 A | 3/1998 | Suzuki et al. |
| 5,728,062 A | 3/1998 | Brisken |
| 5,733,315 A | 3/1998 | Burdette et al. |
| 5,735,280 A | 4/1998 | Sherman et al. |
| 5,735,796 A | 4/1998 | Granz et al. |
| 5,738,635 A | 4/1998 | Chapelon et al. |
| 5,743,862 A | 4/1998 | Izumi |
| 5,743,863 A | 4/1998 | Chapelon |
| 5,746,224 A | 5/1998 | Edwards |
| 5,759,154 A | 6/1998 | Hoyns |
| 5,759,162 A | 6/1998 | Oppelt et al. |
| 5,762,066 A | 6/1998 | Law et al. |
| 5,769,086 A | 6/1998 | Ritchart et al. |
| 5,769,790 A | 6/1998 | Watkins et al. |
| 5,771,896 A | 6/1998 | Sliwa et al. |
| 5,776,092 A | 7/1998 | Farin et al. |
| 5,779,643 A | 7/1998 | Lum et al. |
| 5,782,764 A | 7/1998 | Werne |
| 5,785,705 A | 7/1998 | Baker |
| 5,788,636 A | 8/1998 | Curley |
| 5,800,379 A | 9/1998 | Edwards |
| 5,807,308 A | 9/1998 | Edwards |
| 5,810,742 A | 9/1998 | Pearlman |
| 5,817,021 A | 10/1998 | Reichenberger |
| 5,817,049 A | 10/1998 | Edwards |
| 5,820,580 A | 10/1998 | Edwards et al. |
| 5,823,962 A | 10/1998 | Schaetzle et al. |
| 5,836,896 A | 11/1998 | Rosenschein |
| 5,840,022 A | 11/1998 | Richter |
| 5,840,031 A | 11/1998 | Crowley |
| 5,860,974 A | 1/1999 | Abele |
| 5,873,828 A | 2/1999 | Fujio et al. |

| | | | |
|---|---|---|---|
| 5,873,845 A | 2/1999 | Cline et al. | |
| 5,873,902 A | 2/1999 | Sanghvi et al. | |
| 5,876,399 A | 3/1999 | Chia et al. | |
| 5,882,302 A | 3/1999 | Driscoll, Jr. et al. | |
| 5,893,835 A | 4/1999 | Witt et al. | |
| 5,895,356 A | 4/1999 | Andrus et al. | |
| 5,897,495 A | 4/1999 | Aida et al. | |
| 5,906,580 A * | 5/1999 | Kline-Schoder et al. | 600/459 |
| 5,928,169 A | 7/1999 | Schatzle et al. | |
| 5,931,805 A | 8/1999 | Brisken | |
| 5,931,848 A | 8/1999 | Saadat | |
| 5,938,600 A | 8/1999 | Van Vaals et al. | |
| 5,938,608 A * | 8/1999 | Bieger et al. | 600/439 |
| 5,944,663 A | 8/1999 | Kuth et al. | |
| 5,964,755 A | 10/1999 | Edwards | |
| 5,976,105 A | 11/1999 | Marcove et al. | |
| 5,979,453 A | 11/1999 | Savage et al. | |
| 5,984,881 A | 11/1999 | Ishibashi et al. | |
| 5,984,882 A | 11/1999 | Rosenschein et al. | |
| 5,987,523 A | 11/1999 | Hind et al. | |
| 5,993,389 A | 11/1999 | Driscoll, Jr. et al. | |
| 5,997,534 A | 12/1999 | Tu et al. | |
| 6,001,069 A | 12/1999 | Tachibana et al. | |
| 6,004,269 A | 12/1999 | Crowley et al. | |
| 6,007,499 A | 12/1999 | Martin et al. | |
| 6,010,531 A | 1/2000 | Donlon et al. | |
| 6,013,031 A | 1/2000 | Mendlein et al. | |
| 6,022,319 A | 2/2000 | Willard et al. | |
| 6,024,718 A | 2/2000 | Chen et al. | |
| 6,024,740 A | 2/2000 | Lesh et al. | |
| 6,030,344 A | 2/2000 | Guracar et al. | |
| 6,039,689 A | 3/2000 | Lizzi | |
| 6,042,556 A | 3/2000 | Beach et al. | |
| 6,050,943 A | 4/2000 | Slayton et al. | |
| 6,053,868 A | 4/2000 | Geistert et al. | |
| 6,059,731 A | 5/2000 | Seward et al. | |
| 6,063,050 A | 5/2000 | Manna et al. | |
| 6,066,123 A | 5/2000 | Li et al. | |
| 6,071,238 A | 6/2000 | Chapelon et al. | |
| 6,071,239 A | 6/2000 | Cribbs et al. | |
| 6,071,279 A | 6/2000 | Whayne et al. | |
| 6,083,159 A | 7/2000 | Driscoll, Jr. et al. | |
| 6,086,535 A | 7/2000 | Ishibashi et al. | |
| 6,086,539 A | 7/2000 | Guracar et al. | |
| 6,088,613 A | 7/2000 | Unger | |
| 6,093,149 A | 7/2000 | Guracar et al. | |
| 6,106,470 A | 8/2000 | Geiser et al. | |
| 6,106,517 A | 8/2000 | Zupkas | |
| 6,110,118 A | 8/2000 | Guracar et al. | |
| 6,112,123 A | 8/2000 | Kelleher et al. | |
| 6,113,558 A | 9/2000 | Rosenschein et al. | |
| 6,117,101 A | 9/2000 | Diederich et al. | |
| 6,128,958 A * | 10/2000 | Cain | 73/626 |
| 6,135,963 A | 10/2000 | Haider | |
| 6,135,971 A * | 10/2000 | Hutchinson et al. | 601/3 |
| 6,138,513 A | 10/2000 | Barabash et al. | |
| 6,149,598 A | 11/2000 | Tanaka | |
| 6,156,029 A | 12/2000 | Mueller | |
| 6,159,207 A | 12/2000 | Yoon | |
| 6,171,248 B1 | 1/2001 | Hossack et al. | |
| 6,176,842 B1 | 1/2001 | Tachibana et al. | |
| 6,183,469 B1 | 2/2001 | Thapliyal et al. | |
| 6,193,664 B1 | 2/2001 | Guracar et al. | |
| 6,193,709 B1 | 2/2001 | Miyawaki et al. | |
| 6,206,843 B1 | 3/2001 | Iger et al. | |
| 6,210,330 B1 | 4/2001 | Tepper | |
| 6,216,704 B1 | 4/2001 | Ingle et al. | |
| 6,217,576 B1 | 4/2001 | Tu et al. | |
| 6,221,014 B1 | 4/2001 | Bauer | |
| 6,231,834 B1 | 5/2001 | Unger et al. | |
| 6,241,677 B1 | 6/2001 | Guracar et al. | |
| 6,246,898 B1 | 6/2001 | Vesely et al. | |
| 6,258,029 B1 | 7/2001 | Guracar et al. | |
| 6,266,552 B1 | 7/2001 | Slettenmark | |
| 6,315,723 B1 | 11/2001 | Robinson et al. | |
| 6,322,511 B1 | 11/2001 | Guracar et al. | |
| 6,340,348 B1 | 1/2002 | Krishnan et al. | |
| 6,340,352 B1 | 1/2002 | Okada et al. | |
| 6,352,532 B1 | 3/2002 | Kramer et al. | |
| 6,361,531 B1 | 3/2002 | Hissong | |
| 6,371,903 B1 | 4/2002 | Blanc et al. | |
| 6,371,973 B1 | 4/2002 | Tepper | |
| 6,379,320 B1 | 4/2002 | Lafon et al. | |
| 6,425,867 B1 | 7/2002 | Vaezy et al. | |
| 6,428,477 B1 * | 8/2002 | Mason | 600/437 |
| 6,440,147 B1 | 8/2002 | Lee et al. | |
| 6,461,314 B1 | 10/2002 | Pant et al. | |
| 6,464,640 B1 | 10/2002 | Guracar et al. | |
| 6,482,178 B1 | 11/2002 | Andrews et al. | |
| 6,488,626 B1 | 12/2002 | Lizzi et al. | |
| 6,488,630 B1 * | 12/2002 | Hand et al. | 600/459 |
| 6,508,774 B1 * | 1/2003 | Acker et al. | 601/2 |
| 6,512,957 B1 | 1/2003 | Witte | |
| 6,521,211 B1 | 2/2003 | Unger et al. | |
| 6,533,726 B1 | 3/2003 | Lizzi et al. | |
| 6,540,700 B1 | 4/2003 | Fujimoto et al. | |
| 6,546,934 B1 | 4/2003 | Ingle et al. | |
| 6,562,033 B2 | 5/2003 | Shah et al. | |
| 6,575,969 B1 | 6/2003 | Rittman et al. | |
| 6,599,245 B1 | 7/2003 | Ma et al. | |
| 6,602,251 B2 | 8/2003 | Burbank et al. | |
| 6,613,004 B1 | 9/2003 | Vitek et al. | |
| 6,618,620 B1 | 9/2003 | Freundlich et al. | |
| 6,626,855 B1 | 9/2003 | Weng et al. | |
| 6,635,054 B2 | 10/2003 | Fjield et al. | |
| 6,638,235 B2 | 10/2003 | Miller et al. | |
| 6,641,579 B1 * | 11/2003 | Bernardi et al. | 606/27 |
| 6,645,202 B1 | 11/2003 | Pless et al. | |
| 6,659,949 B1 | 12/2003 | Lang et al. | |
| 6,669,638 B1 | 12/2003 | Miller et al. | |
| 6,673,019 B2 | 1/2004 | Kamiyama | |
| 6,682,483 B1 * | 1/2004 | Abend et al. | 600/437 |
| 6,702,745 B1 | 3/2004 | Smythe | |
| 6,716,184 B2 | 4/2004 | Vaezy et al. | |
| 6,719,694 B2 | 4/2004 | Weng et al. | |
| 6,726,677 B1 | 4/2004 | Flaherty et al. | |
| 6,764,488 B1 | 7/2004 | Burbank et al. | |
| 6,770,070 B1 | 8/2004 | Balbierz | |
| 6,887,239 B2 | 5/2005 | Elstrom et al. | |
| 6,902,536 B2 | 6/2005 | Manna et al. | |
| 6,921,371 B2 | 7/2005 | Wilson | |
| 6,936,024 B1 | 8/2005 | Houser | |
| 6,936,048 B2 | 8/2005 | Hurst | |
| 6,974,417 B2 | 12/2005 | Lockwood et al. | |
| 7,035,166 B2 * | 4/2006 | Zimmerman et al. | 367/88 |
| 7,037,306 B2 | 5/2006 | Podany | |
| 7,063,666 B2 | 6/2006 | Weng et al. | |
| 7,078,015 B2 | 7/2006 | Unger | |
| 7,410,469 B1 | 8/2008 | Talish et al. | |
| 2001/0007940 A1 | 7/2001 | Tu et al. | |
| 2001/0014805 A1 | 8/2001 | Burbank et al. | |
| 2001/0037073 A1 | 11/2001 | White et al. | |
| 2002/0065512 A1 | 5/2002 | Fjield et al. | |
| 2002/0068934 A1 | 6/2002 | Edwards et al. | |
| 2002/0087081 A1 | 7/2002 | Serrano et al. | |
| 2002/0087803 A1 | 7/2002 | Jones et al. | |
| 2002/0111662 A1 | 8/2002 | Iaizzo et al. | |
| 2002/0165579 A1 | 11/2002 | Burbank et al. | |
| 2002/0183371 A1 | 12/2002 | Gordeev et al. | |
| 2002/0183742 A1 | 12/2002 | Carmel et al. | |
| 2002/0193731 A1 | 12/2002 | Myers et al. | |
| 2003/0004434 A1 | 1/2003 | Greco et al. | |
| 2003/0013960 A1 | 1/2003 | Makin et al. | |
| 2003/0013971 A1 | 1/2003 | Makin et al. | |
| 2003/0014093 A1 | 1/2003 | Makin | |
| 2003/0018266 A1 | 1/2003 | Makin et al. | |

| | | | |
|---|---|---|---|
| 2003/0018358 | A1 | 1/2003 | Saadat |
| 2003/0028111 | A1 | 2/2003 | Vaezy et al. |
| 2003/0040698 | A1 | 2/2003 | Makin et al. |
| 2003/0047582 | A1 | 3/2003 | Sonnenschein et al. |
| 2003/0073907 | A1 | 4/2003 | Taylor |
| 2003/0109786 | A1 | 6/2003 | Irioka et al. |
| 2003/0120270 | A1 | 6/2003 | Acker |
| 2003/0120306 | A1 | 6/2003 | Burbank et al. |
| 2003/0144593 | A1 | 7/2003 | Whitmore et al. |
| 2003/0212331 | A1 | 11/2003 | Fenton et al. |
| 2003/0212332 | A1 | 11/2003 | Fenton et al. |
| 2003/0220568 | A1 | 11/2003 | Hansmann et al. |
| 2004/0006336 | A1 | 1/2004 | Swanson |
| 2004/0030268 | A1 | 2/2004 | Weng et al. |
| 2004/0041880 | A1 | 3/2004 | Ikeda et al. |
| 2004/0106870 | A1 | 6/2004 | Mast |
| 2004/0127791 | A1 | 7/2004 | Mast et al. |
| 2004/0143252 | A1 | 7/2004 | Hurst |
| 2005/0015107 | A1 | 1/2005 | O'Brien |
| 2005/0131298 | A1* | 6/2005 | Cai ............................ 600/447 |
| 2005/0137520 | A1 | 6/2005 | Rule et al. |
| 2005/0228286 | A1 | 10/2005 | Messerly et al. |
| 2005/0240125 | A1 | 10/2005 | Makin et al. |
| 2005/0261585 | A1 | 11/2005 | Makin et al. |
| 2005/0261587 | A1 | 11/2005 | Makin et al. |
| 2005/0261588 | A1 | 11/2005 | Makin et al. |
| 2005/0261610 | A1* | 11/2005 | Mast et al. ..................... 601/2 |
| 2005/0267488 | A1 | 12/2005 | Hare et al. |
| 2006/0052701 | A1 | 3/2006 | Carter et al. |
| 2006/0173348 | A1 | 8/2006 | Wilser et al. |
| 2006/0235306 | A1 | 10/2006 | Cotter et al. |
| 2007/0004984 | A1 | 1/2007 | Crum et al. |
| 2007/0021691 | A1 | 1/2007 | Nita et al. |

FOREIGN PATENT DOCUMENTS

| | | |
|---|---|---|
| JP | 04-307044 | 10/1992 |
| JP | 08-084470 | 3/1996 |
| JP | 08-084740 | 4/1996 |
| JP | 9-098980 | 4/1997 |
| JP | 09-192139 | 7/1997 |
| JP | 10-14967 | 1/1998 |
| JP | 10-216146 | 8/1998 |
| JP | 10-511477 | 11/1998 |
| JP | 11-313832 | 11/1999 |
| JP | 2000-116657 | 4/2000 |
| JP | 2000-126185 | 5/2000 |
| JP | 2000-126197 | 5/2000 |
| JP | 2000-237205 | 9/2000 |
| JP | 2001-104358 | 4/2001 |
| WO | 95/29737 | 11/1995 |
| WO | 97/29709 | 8/1997 |
| WO | 98/58588 | 12/1998 |
| WO | 99/33500 | 7/1999 |
| WO | 2000/38580 | 7/2000 |
| WO | 01/34018 | 5/2001 |
| WO | 01/43641 | 6/2001 |
| WO | 01/45550 | 6/2001 |
| WO | WO 01/45550 A2 | 6/2001 |
| WO | 01/97702 | 12/2001 |
| WO | 03/075711 | 9/2003 |
| WO | 03/075771 | 9/2003 |
| WO | 2005/058138 | 6/2005 |
| WO | 2005/072084 | 8/2005 |

OTHER PUBLICATIONS

Hill, C.R. et al., Lesion Development In Focused Ultrasound Surgery: A General Model, Ultrasound in Med. & Biol., 1994, pp. 259-269, vol. 20, No. 3, Elsevier Science Ltd, New York, USA.

Clare, M.C. et al., MRI Guided Focused Ultrasound Surgery (FUS) of uterine leiomyomas: A Feasibility Study, Workshop on MRI-Guided: Focused Ultrasound Surgery, 2002, Syllabus, International Society for Magnetic Resonance in Medicine.

Vaezy, S. et al., Treatment Of Uterine Fibroid Tumors In A Nude Mouse Model Using High-Intensity Focused Ultrasound, Am J Obstet Gynecol, 2000, pp. 6-11, vol. 183, No. 1.

Cool-tip™ RF Tadio Frequency Ablation System, web page from radionics.com.

Electrosurgical Devices, RF Generator and RITA Base Software, web pages from ritamedical.com.

EP, Partial Search Report, European Application No. 04814036.2 (Apr. 3, 2009).

AU, Examiners Report, Australian Application No. 2002312084 (Sep. 26, 2005).

AU, Examiners Report, Australian Application No. 2002310089 (Oct. 20, 2005).

AU, Examiners Report, Australian Application No. 2002303862 (Nov. 25, 2005).

AU, Examiners Report, Australian Application No. 2002314817 (Sep. 22, 2005).

AU, Examiners Report, Australian Application No. 2002305713 (Jan. 31, 2006).

CA, Office Action, Canadian Application No. 2,449,568 (Jan. 31, 2008).

CA, Office Action, Canadian Application No. 2,448,906 (Jan. 31, 2008).

CA, Office Action, Canadian Application No. 2,449,062 (Jan. 31, 2008).

Cain, C.A. et al., "Concentric-Ring and Sector-Vortex Phased-Array Applicators for Ultrasound Hyperthermia," *IEEE Transactions on Microwave Theory and Techniques*, vol. MTT-34, No. 5, pp. 542-551 (May 1986).

Chavrier, F. et al., "Modeling of high-intensity focused ultrasound-induced lesions in the presence of cavitation bubbles," *J. Acoust. Soc. Am.*, 108 (1), pp. 432-440 (Jul. 2000).

Daum, D.R. et al., "Thermal Dose Optimization Via Temporal Switching in Ultrasound Surgery," *IEEE Transactions on Ultrasonics, Ferroelectrics, and Frequency Control*, vol. 45, No. 1, pp. 208-215 (Jan. 1998).

EP, Supplementary Partial European Search Report, European Application No. 04811946.5 (Oct. 30, 2008).

Maass-Moreno, R. et al., "Noninvasive temperature estimation in tissue via ultrasound echo-shifts. Part I. Analytical model," *J. Acoust. Soc. Am.*, 100 (4), Pt. 1, pp. 2514-2521 (Oct. 1996).

Maass-Moreno, R. et al., "Noninvasive temperature estimation in tissue via ultrasound echo-shifts. Part II. *In vitro* study," *J. Acoust. Soc. Am.*, 100 (4), Pt. 1, pp. 2522-2530 (Oct. 1996).

McGough, R.J. et al., "Mode scanning: heating pattern synthesis with ultrasound phased arrays," *Int. J. Hyperthermia*6, 1994, vol. 10, No. 3, pp. 433-442.

PCT, International Search Report, International Application No. PCT/US02/16695 (dated Sep. 24, 2002; published Dec. 5, 2002).

PCT, International Preliminary Examination Report, International Application No. PCT/US02/16695 (Nov. 13, 2002).

PCT, International Search Report, International Application No. PCT/US02/16512 (dated Jul. 17, 2003; published Sep. 25, 2003).

PCT, International Preliminary Examination Report, International Application No. PCT/US02/16512 (Sep. 8, 2003).

PCT, International Search Report, International Application No. PCT/US02/16699 (dated Jul. 17, 2003; published Nov. 20, 2003).

PCT, International Preliminary Examination Report, International Application No. PCT/US02/16699 (Aug. 25, 2003).

PCT, International Search Report, International Application No. PCT/US02/16700 (dated Apr. 15, 2003; published 70/24/2003).

PCT, International Preliminary Examination Report, International Application No. PCT/US02/16700 (May 30, 2004).

PCT, International Search Report, International Application No. PCT/US02/16696 (dated Apr. 4, 2003; published Nov. 6, 2003).

PCT, International Preliminary Examination Report, International Application No. PCT/US02/16696 (May 5, 2003).

PCT, International Search Report, International Application No. PCT/US02/16421 (dated Apr. 4, 2003; published Mar. 18, 2004).

PCT, International Preliminary Examination Report, International Application No. PCT/US02/16421 (May 19, 2003).

PCT, International Search Report, International Application No. PCT/US02/16697 (dated Mar. 31, 2003; published Nov. 6, 2003).

PCT, International Preliminary Examination Report, International Application No. PCT/US02/16697 (Apr. 23, 2003).
PCT, International Search Report, International Application No. PCT/US02/16417 (dated Mar. 26, 2003; published Mar. 11, 2004).
PCT, International Preliminary Examination Report, International Application No. PCT/US02/16417 (May 2, 2003).
PCT, International Search Report, International Application No. PCT/US02/16689 (dated Dec. 18, 2002; published Apr. 17, 2003).
PCT, International Preliminary Examination Report, International Application No. PCT/US02/16689 (Feb. 19, 2003).
Seip, R. et al., "Comparison of Split-Beam Transrectal Prostate Hifu Treatments," Transducer Geometries and Excitation Configurations for 2001 *IEEE Ultrasonics Symposium*, pp. 1343-1346.
Seip, R. et al., "Noninvasive Real-Time Multipoint Temperature Control for Ultrasound Phased Array Treatments," *IEEE Transactions on Ultrasonics, Ferroelectrics, and Frequency Control*, vol. 43, No. 6, pp. 1063-1073 (Nov. 1996).
Simon, C. et al., "Two-Dimensional Temperature Estimation Using Diagnostic Ultrasound," *EEE Transactions on Ultrasonics, Ferroelectrics, and Frequency Control*, vol. 45, No. 4, pp. 1088-1099 (Apr. 1998).
U.S. Appl. No. 10/152,766 and the prosecution history thereof.
U.S. Appl. No. 10/152,769 and the prosecution history thereof.
U.S. Appl. No. 10/153,122 and the prosecution history thereof.
U.S. Appl. No. 10/153,241 and the prosecution history thereof.
U.S. Appl. No. 10/153,245 and the prosecution history thereof.
U.S. Appl. No. 10/153,510 and the prosecution history thereof.
U.S. Appl. No. 10/721,034 and the prosecution history thereof.
U.S. Appl. No. 10/735,045 and the prosecution history thereof.
U.S. Appl. No. 10/795,680 and the prosecution history thereof.
U.S. Appl. No. 10/850,984 and the prosecution history thereof.
U.S. Appl. No. 12/145,635 and the prosecution history thereof.

* cited by examiner

SYSTEM AND METHOD FOR ULTRASOUND THERAPY USING GRATING LOBES

FIELD OF THE INVENTION

The present invention relates generally to ultrasound, and more particularly, to an apparatus and method for providing medical treatment using high-intensity focused ultrasound.

BACKGROUND OF THE INVENTION

Sound waves that have a frequency greater than approximately 20 kHz are referred to in the art as "ultrasound." In the medical field, ultrasound waves are useful for both diagnostic and therapeutic applications. Medical diagnostic ultrasound systems are useful for generating images of anatomical structures within a target area of a patient's body. The images are obtained by scanning a target area with waves of ultrasound energy. In therapeutic ultrasound applications, high intensity ultrasound energy is transmitted into a target area to induce changes in state of the target. High-intensity focused ultrasound ("HIFU") pulses induce changes in tissue state through thermal effects (e.g., induced hyperthermia) and mechanical effects (e.g., induced cavitation).

The use of high intensity focused ultrasound to eliminate tissue or to alter the characteristics of tissue at a target location, volume, region or area within a larger mass, body or area of anatomical tissue presents many advantages, including minimization of trauma and pain for the patient, elimination of the need for a surgical incision, stitches and exposure of internal tissue, avoidance of damage to tissue other than that which is to be treated, altered or removed, lack of a harmful cumulative effect from the ultrasound energy on the surrounding non-target tissue, reduction in treatment costs, elimination of the need in many cases for general anesthesia, reduction of the risk of infection and other complications, avoidance of blood loss, and the ability for high intensity focused ultrasound procedures to be performed in non-hospital sites and/or on an out-patient basis.

In high-intensity focused ultrasound hyperthermia treatments, intensity of ultrasonic waves generated by a highly focused transducer increases from the source to the region of focus where it can reach a very high temperature. The absorption of the ultrasonic energy at the focus induces a sudden temperature rise of tissue, which causes ablation of the target volume of cells in the focal region. Thus, as an example, HIFU hyperthermia treatments can cause necrotization of an internal lesion without damage to the intermediate tissues. The focal region dimensions are referred to as the depth of field, and the distance from the transducer to the center point of the focal region is referred to as the depth of focus. Ultrasound is a promising non-invasive surgical technique because the ultrasonic waves provide effective penetration of intervening tissues, yet with sufficiently low attenuation to deliver energy to a small focal target volume. Currently there is no other known modality that offers noninvasive, deep, localized focusing of non-ionizing radiation for therapeutic purposes. Thus, ultrasonic treatment has a great advantage over electromagnetic and radioactive therapeutic treatment techniques.

The beam emitted by a single ultrasound focused transducer element is generally effective within a fixed region, called the "focal zone." This focal zone frequently is smaller than the size of the target tissue. Treatment of extensive targets is consequently a problem. A solution to this shortcoming is to utilize a transducer comprising a plurality of individual transducer elements arranged closely together to form an array. These arrays are focused at the desired treatment site through a combination of geometric and electronic focusing. Geometric focusing is determined by the permanent geometry of the array, while electronic focusing involves the use of phase delays and wave interference to achieve constructive interference at the target tissue. Electronic focusing allows movement of the treatment location without the need for mechanical movement of the array.

A particular problem is the use of small ultrasound arrays in relation to certain types of medical treatments, such as HIFU treatment in association with laparoscopic, percutaneous, and interstitial procedures. Individual focused transducer elements are often smaller than the target tissue, requiring movement of the transducer to ablate the tissue. The use of transducer arrays is likewise problematic, since the space available for placement or insertion of the transducer is limited.

HIFU treatment using a small focal point, whether generated from a single ultrasound transducer element or a phased array, allows great treatment selectivity. For example, the focal spot can be used to treat particular regions of tissue while sparing critical tissue structures. However, focused transducers are slow when used to treat large volumes of tissue. It is desirable to provide an ultrasound transducer that is capable of providing a small, selective focal spot for treating a specific region of tissue and is also capable of treating large volumes of tissue.

A potential solution is the use of a physically small array having fewer transducer elements, wherein the elements can be electronically controlled to focus or steer the beam. A conventional ultrasound transducer array used for beam forming typically requires small transducer elements having an aperture pitch that is half the wavelength of the ultrasound signal or less. Ultrasound arrays for use in confined spaces preferably have larger transducer elements of two or more wavelengths in aperture pitch for effective ablation. Conventional methods of focusing and beam steering are not compatible with these transducers. When an electronic focus is attempted with such a transducer, large secondary off-axis foci, or "grating lobes" are created. These grating lobes are comparable in amplitude to the primary focus and draw energy from the main focal lobe, reducing the efficacy of the ultrasound beam.

Another potential solution is to use an unfocused ultrasound transducer. An unfocused ultrasound transducer will treat a larger portion of the target tissue. However, the ablation depth may be substantially reduced in relation to a focused ultrasound beam, necessitating more movement of the transducer during the ablation procedure.

Still, scientists and engineers continue to seek improved methods for therapeutic ultrasound medical treatment of tissue. There is a need for a physically small ultrasound array that is capable of treating a relatively large portion of target tissue with a greater ablation depth than is currently available in the art.

SUMMARY OF THE INVENTION

One embodiment of the present invention overcomes the aforementioned limitations of ultrasound transducers by altering the phasing of transducer elements on a transducer array, such as a linear ultrasound array, so that the positions of grating lobes emitted by the array can be changed. A volume of target tissue can be ablated using a sequence of several different insonifications. Each of these insonifications creates multiple grating lobe foci to cover a different subset of the volume. In this manner, ablation of a large target tissue can be accomplished more efficiently than is possible using a single focus without grating lobes.

An embodiment of the present invention is a system for medical treatment of tissue using ultrasound. The system comprises a probe having an array of transducer elements; an ultrasound waveform generator adapted to generate at least one electrical ultrasound signal; and a plurality of phase controls coupled to the ultrasound waveform generator, each phase control adapted to generate from the at least one electrical ultrasound signal a phase-shifted drive signal that is coupled to an associated transducer element. The drive signals are effective to control grating lobe foci emitted by the array.

Another embodiment of the present invention is a system for medical treatment of tissue using ultrasound. The system comprises a probe having an array of transducer elements; an ultrasound waveform generator adapted to generate at least one electrical ultrasound signal; and a plurality of phase controls coupled to the ultrasound waveform generator, each phase control adapted to generate from the at least one electrical ultrasound signal a drive signal that is coupled to an associated transducer element. The phase controls comprise a focusing phase shift portion adapted to produce a first phase shift in the drive signal, and a grating lobe phase shift portion adapted to produce a second phase shift in the drive signal, wherein each drive signal has a composite phase shift that is the mathematical sum of the first and second phase shifts. The drive signals are effective to cause the array to emit acoustic ultrasound signals having a focal point controlled by the first phase shift and grating lobe foci controlled by the second phase shift.

A method of the present invention is for medically treating tissue using ultrasound. The method comprises the steps of providing a probe having an array of transducer elements, generating at least one electrical ultrasound signal, generating from the at least one electrical ultrasound signal a plurality of phase-shifted drive signals, and coupling each phase-shifted drive signal to an associated transducer element. The drive signals are effective to control grating lobe foci emitted by the array.

DETAILED DESCRIPTION OF THE INVENTION

Figure 1:
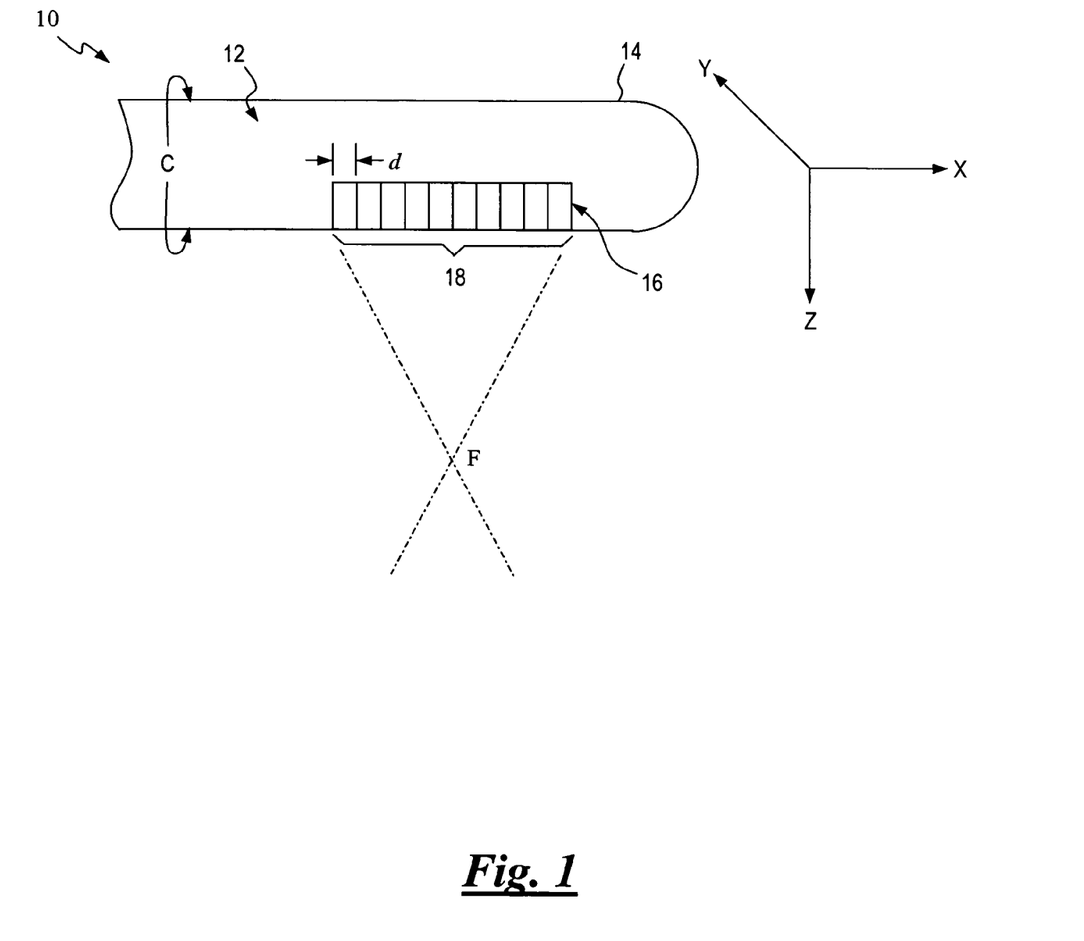
FIG. 1 is a is a schematic view of the distal portion of an ultrasound treatment probe according to an embodiment of the present invention.

Referring now to the Figures, in which like numerals indicate like elements, FIG. 1 is a schematic view of a distal portion of an embodiment of an ultrasound treatment probe 10 that includes a body 12 in the form of a longitudinal shaft having a circumference C. Body 12 has a distal end region 14 which includes a substantially linear ultrasonic transducer array 16 having a plurality of transducer elements 18 that produce acoustic ultrasound signals used to medically treat tissue.

Probe 10 may have various configurations for various uses. For example, probe 10 may be used for laparoscopic, percutaneous and interstitial use for tissue ablation. The particular shape of probe 10 will be dictated by its use and FIG. 1 is merely intended to generally represent the distal end portion of probe 10, which typically is a cylindrical shaft. One skilled in the art will recognize that the present invention is not limited to such a configuration and may be applied to other types of arrays including, without limitation, curved arrays and collections of larger, separate transducer elements on a single probe that are focused, planar, or convex in curvature. A lens or acoustic window (not shown for clarity) may cover the emitting faces of linear transducer array 16.

With continued reference to FIG. 1, to focus a transducer array 16 having a plurality of transducer elements 18, a pitch d, and generating ultrasound at a wavelength $\lambda$, the array elements are phased to focus at a focal distance F. The electronic signals applied to each transducer element are separately phase shifted so that the propagating waves emitted by each element combine constructively at the focal point. These phase shifts are equivalent to time delays of the signals applied to the transducer elements. In the XZ plane of FIG. 1, foci of acoustic ultrasound signals will appear at approximate azimuthal positions X given by Equation 1:

$$\text{Foci}(X) = \frac{F\lambda m}{d} \qquad \text{Equation 1}$$

where m=0, ±1, ±2 . . . .

Figure 2:
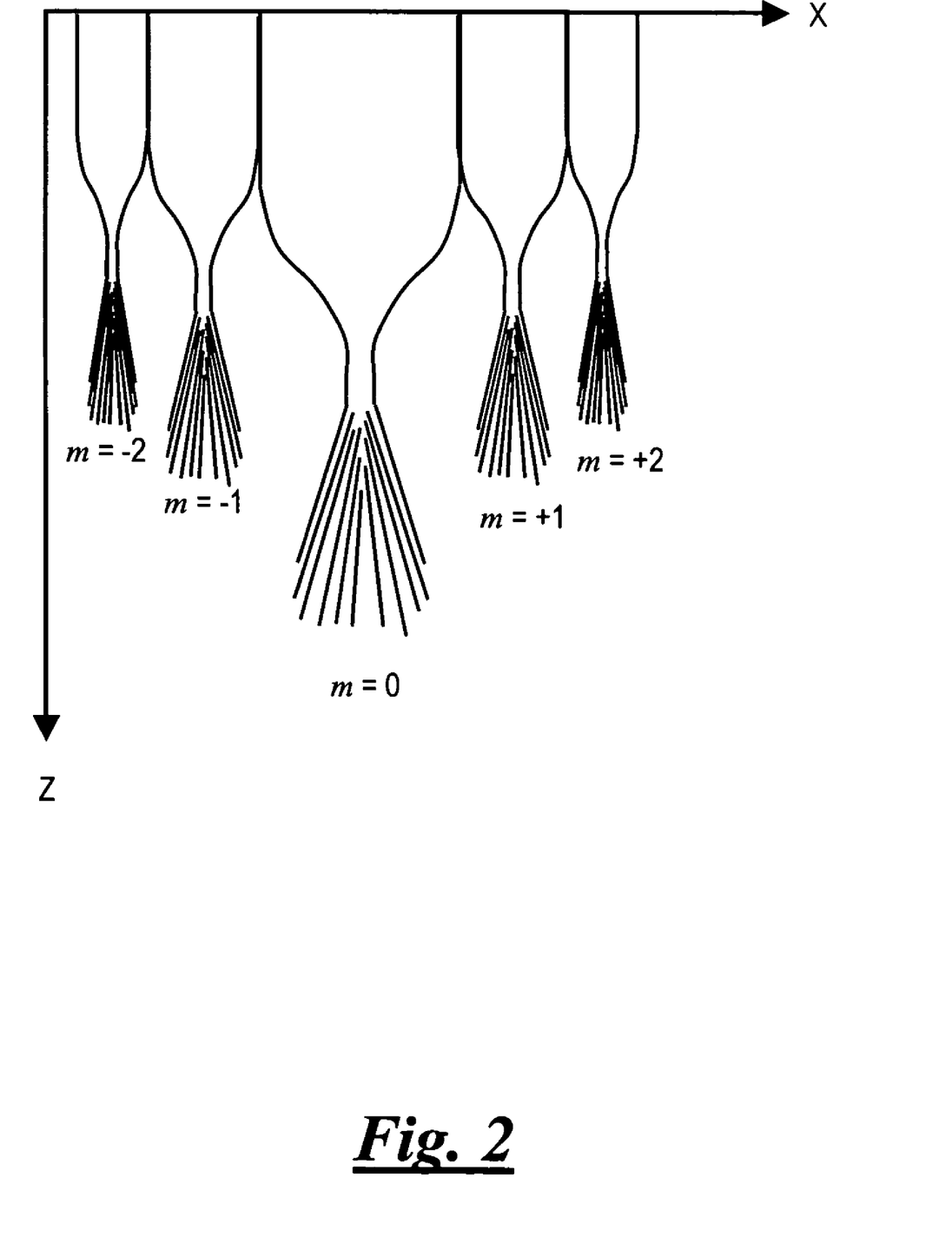
FIG. 2 is a representation of the acoustic pressure amplitude of ultrasound waves emitted by the probe of FIG. 1.

With the exception of m=0, which is the main lobe or central focus, these maxima are grating lobes and are normally an undesired characteristic of linear transducer arrays. An example illustration of the acoustic amplitude of an ultrasound transducer array 16 exemplifying foci of Equation 1 is shown in FIG. 2. FIG. 2 illustrates the relative spatial positions of the maxima.

An additional phase factor $\Phi$ may be expressed by Equation 2:

$$\Phi = e^{\frac{i2\pi n}{N}} \qquad \text{Equation 2}$$

If phase factor $\Phi$ is applied to all elements 18 of array 16, where n is an element index, grating lobes will appear at the approximate positions given by Equation 3:

$$\text{Foci} = \frac{F\lambda\left(m + \frac{1}{N}\right)}{d} \qquad \text{Equation 3}$$

For example, if N=2 in Equation 2, the phase shift between adjacent elements 18 will be 180°, corresponding to a reversal of polarity between elements. As a result, grating lobes will occur approximate positions defined by Equation 4:

$$\text{Foci} = \frac{F\lambda\left(m + \frac{1}{2}\right)}{d} \quad \text{Equation 4}$$

Figure 3:
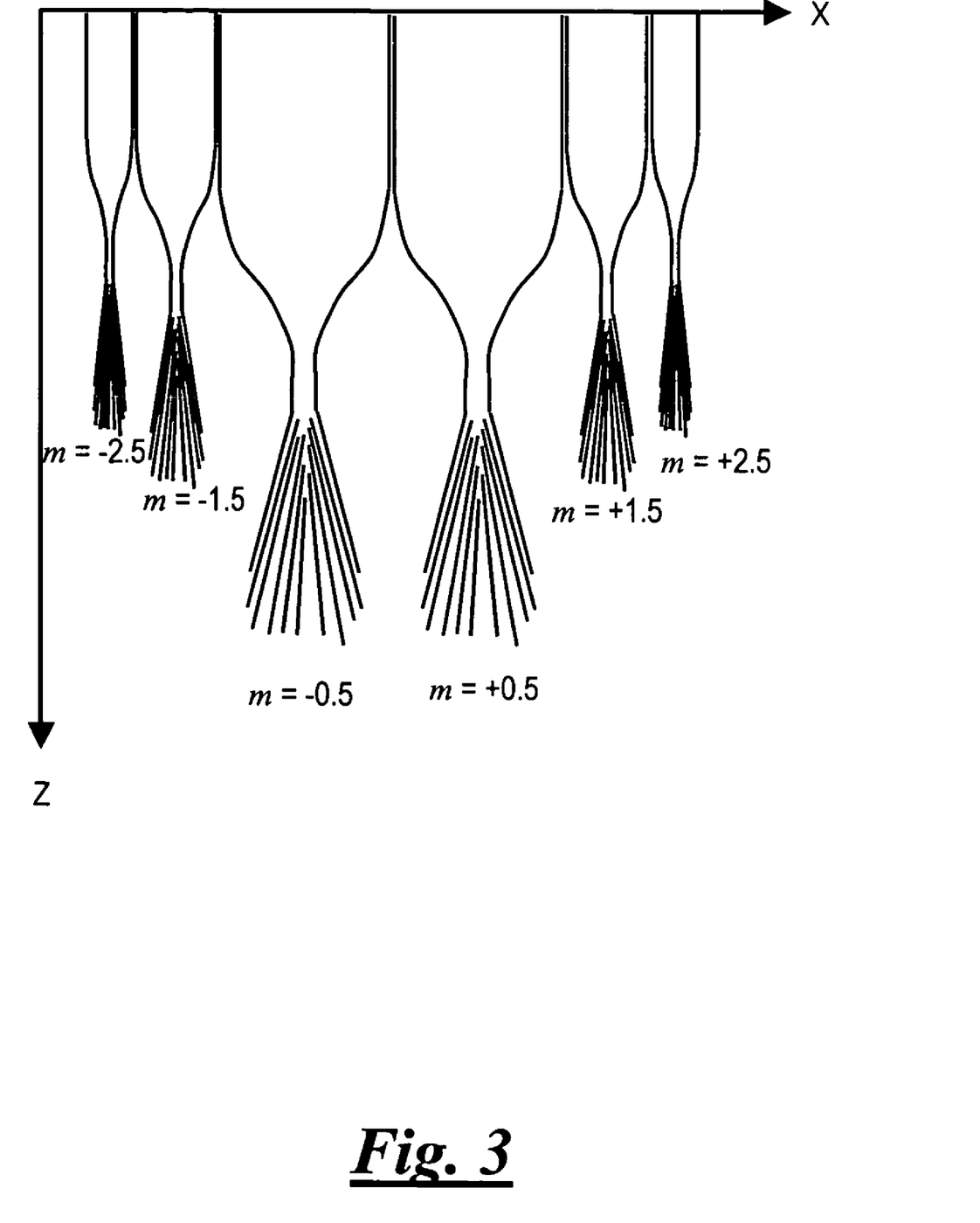
FIG. 3 is another representation of the acoustic pressure amplitude of ultrasound waves emitted by the probe of FIG. 1.

As can be seen, grating lobes will occur at positions about halfway between lobes generated in accordance with Equation 1. An example illustration of the acoustic field from a group of ultrasound elements 18 focused at the distance Z=F (see FIG. 1) and additionally phased according to Equation 2 with N=2 is shown in FIG. 3.

In an embodiment of the present invention, an element-dependent phase factor $\Phi$ is applied to the electrical ultrasound signal applied to each transducer element 18, in addition to the phase factor associated with electronic focusing. The element-dependent phase factor $\Phi$ causes grating lobe foci to shift in position corresponding to Equation 3. Multiple insonifications using different element-dependent phase factors can cause tissue heating in multiple locations corresponding to the different spatial patterns of grating lobe foci. As a result, heat is deposited in a larger volume of tissue as compared to heating generated with an acoustic ultrasound signal according to Equation 1. The heating of a greater area is represented graphically by FIG. 4, wherein a composite of the insonification patterns of FIGS. 2 and 3 in combination causes tissue heating within a greater region than is possible with the insonifications shown in FIG. 2 or FIG. 3 alone. In one embodiment of the present invention the insonified medium may be tissue to be medically treated.

Figure 5:
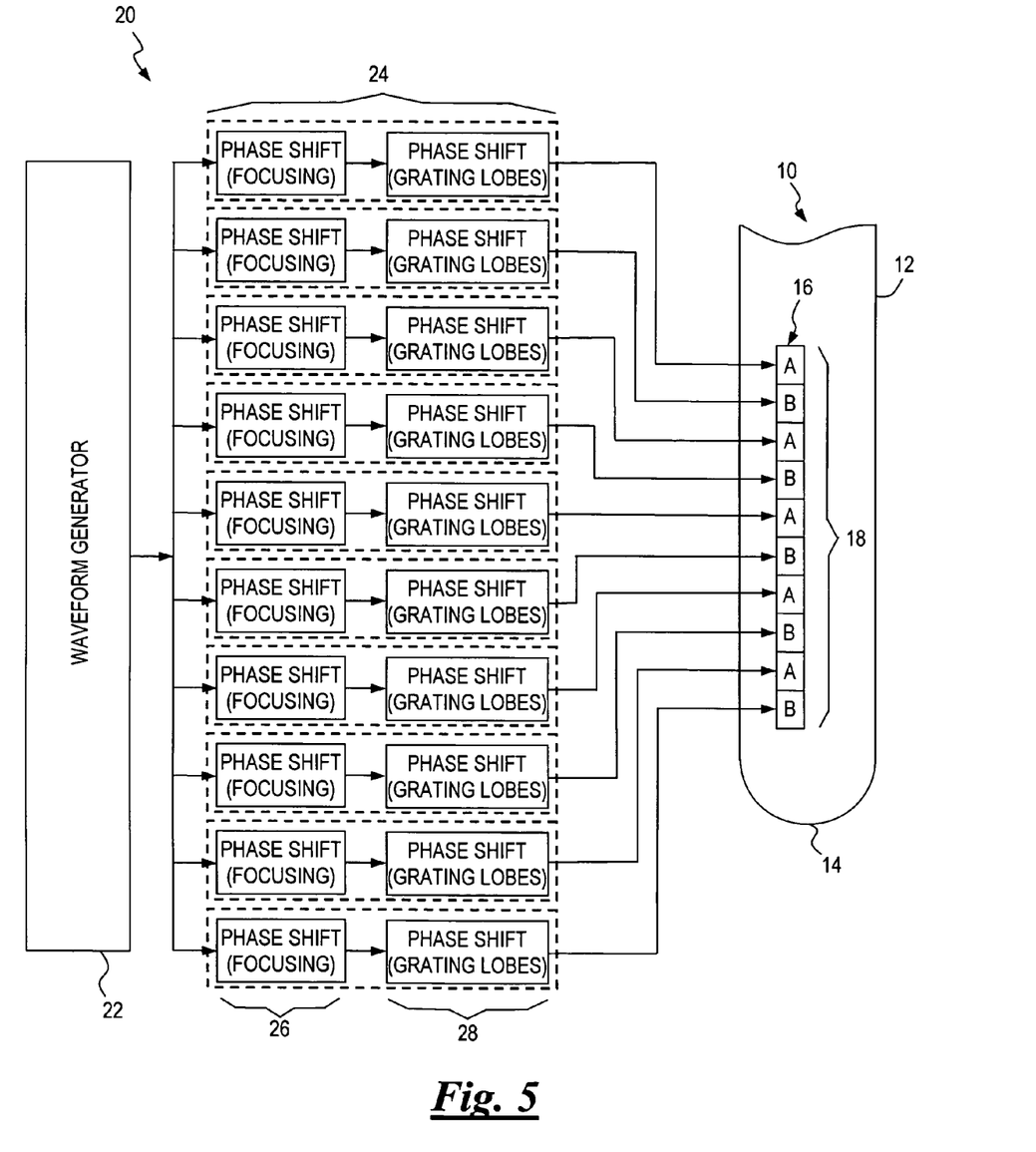
FIG. 5 is a schematic block diagram of a medical ultrasound therapeutic treatment system according to an embodiment of the present invention.

An example ultrasound treatment system 20 according to an embodiment of the present invention is depicted in FIG. 5. Ultrasound treatment system 20 includes an ultrasound treatment probe 10, a waveform generator 22, and a plurality of phase controls 24.

Ultrasound treatment probe 10 includes a transducer array 16 having a plurality of transducer elements 18. In the example of FIG. 5, transducer array 16 may include two groups of elements, labeled "A" and "B," arranged in an alternating pattern between adjacent elements.

Waveform generator 22 generates at least one electrical ultrasound signal having a predetermined amplitude, frequency and impedance compatible with transducer elements 18. Waveform generator 22 may have either a plurality of outputs or a single output for the electrical ultrasound signal.

A plurality of phase controls 24 are coupled to waveform generator 22 and are adapted to receive the electrical ultrasound signal. Each phase control 24 generates from the electrical ultrasound signal a drive signal adapted to drive an associated element 18 of array 16. Phase controls 24 each include a focusing phase shift portion 26 that produces a first phase shift in the drive signal, the first phase shift being adapted to drive an associated transducer element 18 such that array 16 emits an electronically focused ultrasound signal.

Each phase control 24 further includes a grating lobe phase shift portion 28. Grating lobe phase shift portion 28 that produces a second phase shift in the drive signal. The second phase shift applies an element-dependent phase factor $\Phi$ (see Equations 2 and 3), effective to control the azimuthal position of grating lobes emitted by array 16 in the manner previously discussed. The drive signal that is coupled from each phase control 24 to an associated element 18 thus has a composite phase shift that is the mathematical sum of the first phase shift, adapted to achieve electronic focusing of array 16, and the second phase shift, adapted to control the position of grating lobes produced by the array.

In various embodiments of the present invention, focusing phase shift portion 26 may be used to electronically focus the acoustic signal of array 16 independently of the relative position of the grating lobes. Likewise, grating lobe phase shift portion 28 may be used to vary the relative locations of grating lobes emitted by array 16 independently of the focused acoustic signal. For example, array 16 may be electronically focused at a single location while a plurality of grating lobe foci are produced at one or more predetermined groups of locations, which may be varied periodically and/or sequentially in number and/or location. Similarly, array 16 may also be electronically focused periodically and/or sequentially at variable locations while a plurality of grating lobe foci are produced at one or more predetermined groups of locations, which may also be varied periodically and/or sequentially in number and/or location.

The composite drive signal produced by each phase control 24 is coupled to an associated transducer element 18 by any conventional means including, without limitation, electrical wires and printed circuits. Each transducer element 18 converts the drive signal to a high-intensity acoustic ultrasound signal. In combination, elements 18 of array 16 form a focused acoustic ultrasound signal having grating lobes in accordance with Equations 1-4, as implemented by controlling the phase shifts produced by focusing phase shift portion 26 and grating lobe phase shift portion 28 of phase control 24.

In operation, waveform generator 22 generates at least one electrical ultrasound signal. The electrical ultrasound signal of waveform generator 22 is coupled to phase controls 24, each of which generate a drive signal having a predetermined composite phase shift that is the mathematical sum of a first phase shift directed to electronic focusing of array 16 and a second phase shift that is directed to manipulating the locations of grating lobe foci according to Equation 2. The drive signals from each phase control 24 are coupled to an associated transducer element 18. Each transducer element 18 converts the drive signal to a high-intensity ultrasound acoustic signal having focusing characteristics and grating lobe positions that correspond with the predetermined phase relationships generated by phase shift portions 26, 28 of phase control 24.

Figure 4:
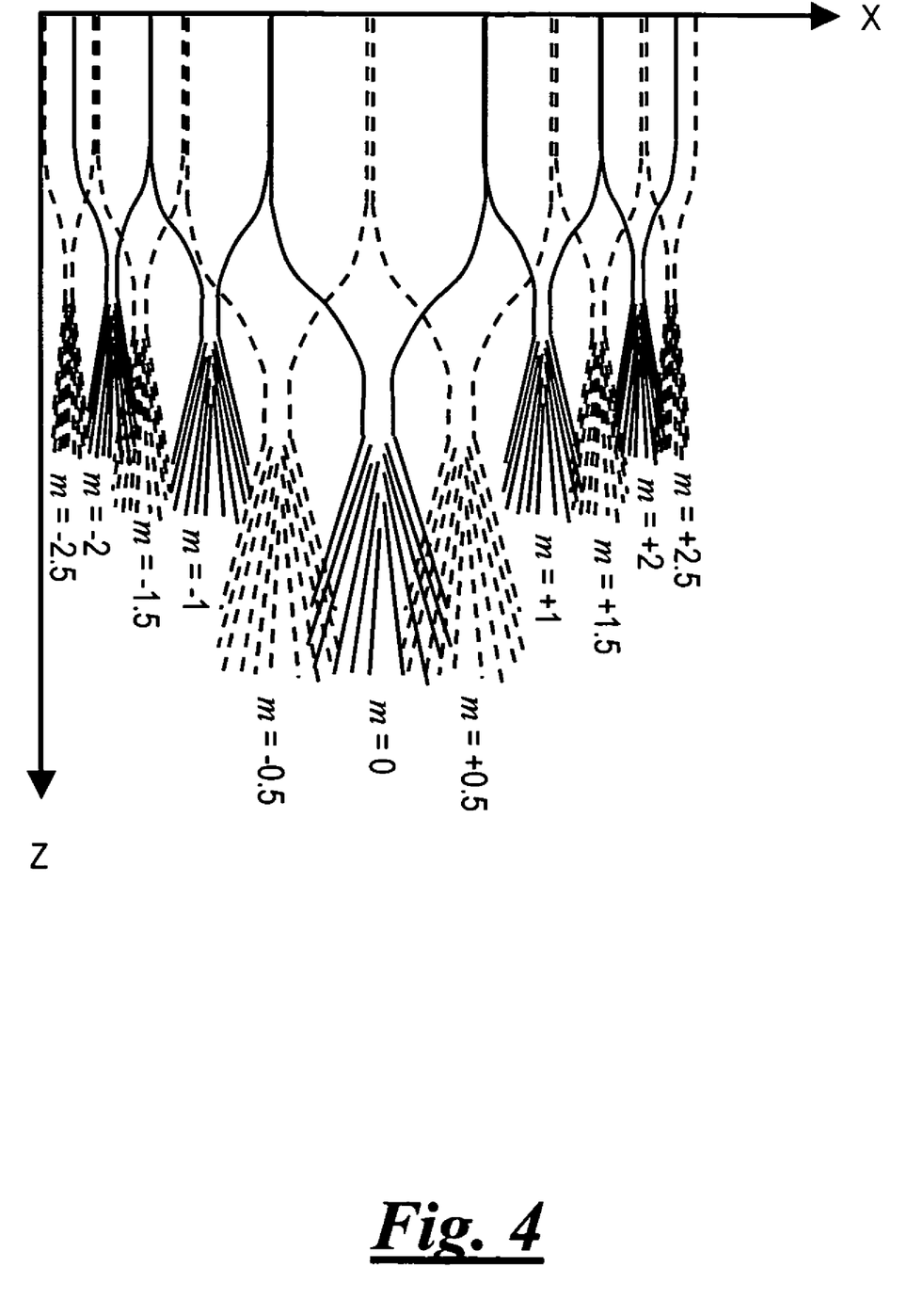
FIG. 4 is a composite representation of the acoustic pressure amplitudes of FIGS. 2 and 3.

Drive signals of phase control 24 may optionally have varying phase-shift patterns to steer grating lobe foci to varying azimuthal positions, such as those illustrated in FIGS. 2 and 3. This is accomplished by periodically or sequentially changing in time the phase shift applied by grating lobe phase shift portions 28 in accordance with multiple element-dependent phase factors $\Phi$ (see Equation 2), resulting in a more uniform ultrasound heating pattern. An example is a composite of the patterns of FIGS. 2 and 3, as depicted in FIG. 4. FIG. 2 represents the ultrasonic field when no grating lobe phase shift is employed (N=1). FIG. 3 represents the ultrasonic field for a grating lobe phase shift determined from Equation 2 using N=2, so that group "A" is driven with a grating lobe phase shift of 0 while group "B" is driven with a grating lobe phase shift of $\pi$ or vice-versa. The composite heating pattern shown in FIG. 4 illustrates that, by applying both grating lobe patterns, a more uniform heating pattern may be achieved by insonifying the medium at spatially interspersed focal locations.

With continued reference to FIG. 5, in an alternate embodiment of the present invention, "N" of Equation 3 may be set to 1 (i.e., no grating lobe phase shift) such that array 16 is focused at a single point and additional heating of tissue occurs at the multiple grating lobe foci. In another alternate embodiment of the present invention, "N" of equation 3 may be set to a value of 2, causing grating lobes to occur at positions differing from N=1. In yet another embodiment of the present invention, any sequence of insonifications using transducer 10 may be implemented with differing or varying "N" values or states in any desirable order, sequence or period of time to produce accordingly differing or varying grating lobe patterns implemented in a predetermined sequence, pattern or characteristic to execute a given treatment plan.

One skilled in the art will recognize that the drive signal generated by phase control 24 may be produced in a number of different ways. For example, focusing phase shift portion 26 and grating lobe phase shift portion 28 may be separate components of ultrasound treatment system 20. In addition, each phase control 24 may mathematically derive and generate a single phase shift representing the sum of phase shifts produced by focusing phase shift portion 26 and grating lobe phase shift portion 28. Phase shift control 24 may utilize a conventional computing device, such as a computer or microprocessor, in conjunction with a predetermined set of instructions, such as a computer program, to mathematically derive the summed phase shift value.

Transducer 14 is not limited to a substantially linear array 16. In various other embodiments of the present invention transducer 14 and array 16 may be any combination of phased arrays, a plurality of single-element transducers having a common drive signal, geometrically focused transducers, and convex transducers. In addition, transducer 14 may optionally include an acoustic lens (not shown), which may or may not act to focus or alter the acoustic signals generated by elements 18.

With reference to FIG. 5, alternate embodiments of the present invention are envisioned wherein the focusing phase factor is not needed. Example embodiments include arrangements where focusing is accomplished in some other way including, without limitation, geometrically focused transducers 10. Further, an acoustic lens may optionally be used to focus the ultrasound acoustic signal. In such embodiments focusing phase shift portion 26 may be deleted from phase control 24.

One skilled in the art will recognize that, for situations when the grating lobes are sufficiently separated, that additional insonifications can be made using various phase factors Φ to fill the gaps between grating lobes and thus deposit heat uniformly throughout the volume of tissue to be treated. For example, insonifications where N of Equation 3 equals ±4 may be used in conjunction with N=±2. Grating lobe foci then appear about halfway between all of the foci created using the original insonification of FIG. 2, with no phase factor Φ, and the second insonification with N=±2. Similarly, various other phase factors Φ can be applied separately or in combination to create other insonifications that deposit heat in other desired patterns.

A particular advantage of the present invention is that treatment planning can be optimized using insonifications with manipulated grating lobe foci. In such optimization, planning aspects such as the duration of each insonification, the power level of each insonification, and the order of insonifications can be altered to provide maximal ablation depth. For example, acoustic screening (due to cavitation and/or tissue boiling) can be minimized because proximal tissue regions heating during one insonification can cool during the next insonification that heats different tissue regions. Other advantages include the ability to treat a large tissue volume rapidly while maintaining selectivity with regard to the regions of tissue to be treated. Since multiple foci may be positioned as required for a predetermined treatment plan, critical tissue structures can be spared and target tissue can be efficiently treated.

With reference again to FIG. 1, maximal power may be delivered into the tissue by using the entire length of transducer array 16. However, if greater specificity is desired, the present invention can be used with appropriate sub-apertures (not shown) to limit the extent of tissue ablation. In addition, if a specific tissue structure (such as a major blood vessel) is to be spared, grating lobe foci can be manipulated as disclosed herein to avoid critical structures while ablating surrounding tissue.

As will be recognized by one skilled in the art, embodiments of the present invention are capable of ablating larger volumes of tissue with greater speed than is currently available, using small-diameter ultrasonic probes suitable for interstitial use in soft tissue. In comparison, prior art swept-focus schemes are much slower and less efficient, especially for small-aperture transducers. Planar exposures ablate tissue at greater rates, but do not achieve ablation depths necessary for practical use. Prior art split-focus schemes increase efficiency of ablation, but require much larger probes and this is inappropriate for interstitial use. Embodiments of the present invention overcome both of these disadvantages.

While the present invention has been illustrated by a description of several methods and embodiments, it is not the intention of the applicants to restrict or limit the spirit and scope of the appended claims to such detail. Numerous other variations, changes, and substitutions will occur to those skilled in the art without departing from the scope of the invention. For instance, the ultrasound methods and systems of the invention have application in therapeutic tissue ablation, taking into account the obvious modifications of such methods, systems and components to be compatible with such an ablation system. It will be understood that the foregoing description is provided by way of example, and that other modifications may occur to those skilled in the art without departing from the scope and spirit of the appended claims.

What is claimed is:

1. A method for medical treatment of tissue using ultrasound, comprising the steps of:
    providing a probe having an array of transducer elements;
    generating at least one electrical ultrasound signal;
    generating from the at least one electrical ultrasound signal a plurality of phase-shifted drive signals;
    coupling each phase-shifted drive signal to an associated transducer element, effective to control grating-lobe foci emitted by the array without changing array steering direction relative to the probe and without changing array focusing relative to the probe;
    electronically focusing the array at a single location;
    producing a plurality of grating-lobe foci only at a first predetermined group of locations for a first period of time for medical treatment of tissue with the array electronically focused at the single location; and
    producing a plurality of grating-lobe foci only at a second predetermined group of locations for a second period of time for medical treatment of tissue with the array electronically focused at the single location, wherein the locations of the second predetermined group of locations are different from the locations of the first predetermined group of locations, and wherein the second period of time occurs later and separate from the first period of time.

2. The method of claim 1, further comprising the step of selecting a transducer that includes at least one of a substantially linear array, a phased array, a curved array, a geometrically focused transducer, a plurality of single-element transducers having a common drive signal, and a convex transducer.

3. The method of claim 2, further comprising the step of adding an acoustic lens to the transducer.

4. The method of claim 1, further comprising the steps of:
forming a plurality of groups of elements;
coupling drive signals that are substantially alike in phase shift to transducer elements within each group; and
substantially differing the phase shifts of drive signals between groups of elements.

5. The method of claim 1, further comprising the step of periodically varying the phase shifts of the drive signals.

6. The method of claim 5, further comprising the step of periodically varying the phase shifts of the drive signals between a plurality of predetermined states.

* * * * *